United States Patent [19]
Hornstein

[11] Patent Number: 4,940,138
[45] Date of Patent: Jul. 10, 1990

[54] CONTAINER WITH COLLAPSIBLE CUP

[75] Inventor: Allan S. Hornstein, Matawan, N.J.

[73] Assignee: Queen City Group, Cincinnati, Ohio

[21] Appl. No.: 472,092

[22] Filed: Jan. 30, 1990

[51] Int. Cl.$^5$ .................. B65D 77/00; B65D 8/14
[52] U.S. Cl. .................... 206/218; 220/8; 220/23; 215/DIG. 7
[58] Field of Search .............. 206/218; 215/DIG. 7; 220/23, 8

[56] References Cited

U.S. PATENT DOCUMENTS

| | | | |
|---|---|---|---|
| 21,955 | 11/1858 | Grosholz | 220/8 |
| 1,128,211 | 2/1915 | Wohlwend | 206/218 |
| 1,184,366 | 5/1916 | Miller | 206/218 |
| 1,724,743 | 8/1929 | Allen | 220/8 |
| 2,076,457 | 4/1937 | Genone | 215/DIG. 7 |
| 2,211,326 | 8/1940 | Gillice | 220/8 |
| 3,285,459 | 11/1966 | Gahm | 206/218 X |

FOREIGN PATENT DOCUMENTS

| | | | |
|---|---|---|---|
| 968799 | 5/1950 | France | 220/8 |
| 1095627 | 12/1954 | France | 220/8 |
| 1173893 | 12/1969 | United Kingdom | 220/8 |

*Primary Examiner*—William I. Price
*Attorney, Agent, or Firm*—Wood, Herron & Evans

[57] ABSTRACT

A cylindrical tube having a removable end closure at a first end and a collapsible drinking cup inserted in a second end is provided as a storage container for miscellaneous items such as first aid components. In its collapsed state, the collapsible drinking cup functions as an end plug for the container and in its extended state, it is a liquid tight cup for use with the container contents.

7 Claims, 1 Drawing Sheet

CONTAINER WITH COLLAPSIBLE CUP

FIELD OF THE INVENTION

The present invention relates to a tubular container which has a collapsible drinking cup as an end closure. The container is especially suited as a repository for first aid items.

BACKGROUND OF THE INVENTION

Small first aid kits are widely kept in homes, automobiles, backpacks and other similar locations. Most of these portable first aid kits have containers which are box-like structures constructed of a light metal or sturdy plastic. The box typically requires a hinge to join a cover to a box base, a latch to secure the unhinged side of the cover and a handle attached to either the cover or the box base for carrying the kit. Each of these items adds to the cost of constructing the container.

The handles of such containers usually require a hinge and pin so the handle will fold flat on the container for storage purposes and swing away from the container for carrying purposes. An additional hinge and pin structure usually joins the cover and the box base. This hinge and pin combination could be eliminated by the use of flexible strips between the cover and base. However, these strips wear easily with little use and greatly reduce the useful life of the container. Similarly, the latch which holds the container closed usually requires one member mounted to the box base and a mating latch member mounted to the cover. This latching mechanism increases the complexity of the container manufacture.

Such box-like kit containers are often awkward or inconvenient to store with other articles. Usually the cover and the base have angular edges which are hardly deformable or conformable when the kit is stored with other objects, as when it is carried in a knapsack or stored in the trunk of an automobile. In the irregular confines of such storage areas, these box-like kits do not permit efficient utilization of the storage area. Accordingly, containers suitable for use with first aid kits and the like which do not utilize a rectangular or box-like shape and which can be produced at lower cost are needed.

In first aid kits which include drinkable liquids or pills which require liquid for ingestion, a drinking cup is an especially useful kit component. A collapsible version of a cup is available which could be included in the container. However, while collapsible cups use less space than non-collapsible cups, they do occupy space in the container which could be used for additional contents. Inclusion of such a cup with a kit container, without using internal container storage space would be a real benefit.

SUMMARY OF THE INVENTION

The present invention provides a non-boxlike container for first aid kits or other small items, and includes a collapsible drinking cup as part of the container structure itself, without complicating its manufacture.

The container of the invention includes a cylindrical plastic tube which is open at both ends. One end of the tube is closed by a cap which preferably has a skirt or rim that frictionally engages the outside of the tube and receives the tube end within the rim of the cap. Articles such as first aid items can then be placed within the tube for storage.

The other end of the tube is closed by a collapsible cup which frictionally fits within the tube as an end plug. The collapsible cup has a flange or rib around its circumference which abuts the tube end and acts as a stop to limit the cup from being too deeply seated within the tube. The flange also provides a gripping surface for removal of the collapsible cup from the tube.

The cup is erected from vertical annular bands of graduated increasing diameters, with the smallest diameter band attached to the cup base. When the cup is collapsed, all the bands concentrically rest against the cup base. When the largest band is pulled away from the cup base the remaining bands form a truncated cone-like vessel for holding liquids. A cover engages the cup base when the cup is collapsed to enclose and protect the annular rings and is removed for cup use.

The cylindrical tube stores easily in irregularly shaped areas and is easy to handle. The end plug and collapsible cup eliminate the need for latching parts and hinges since they frictionally fit within the tube. Use of the collapsible cup as a tube end closure also frees internal container space for storage of other items.

These and other advantages and features of the present invention will be apparent from the summary description above and the detailed description below.

DESCRIPTION OF THE PREFERRED EMBODIMENT

Figure 1:
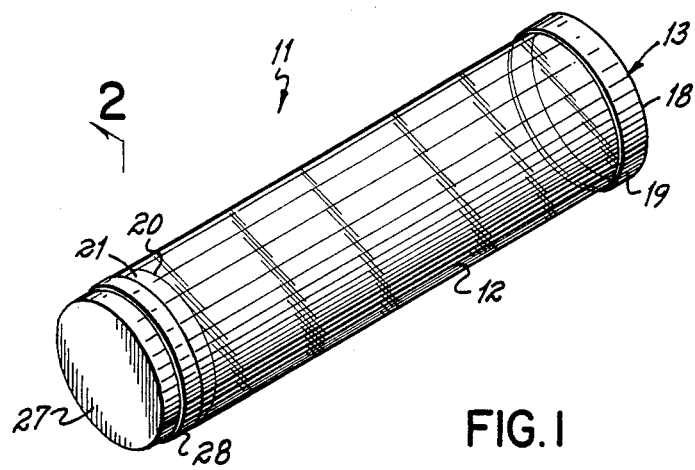
FIG. 1 is a perspective of a closed container in accordance with a preferred embodiment of the invention, showing an end of the container closed by a collapsible drinking cup.

Referring to FIG. 1, a preferred form of container 11 embodying the present invention is shown. The container 11 includes a cylindrical tube 12 which is closed at a first end by a removable cap or closure 13 and closed at a second end by a removable drinking cup 14 mounted in collapsed condition. The length and diameter of tube 12 are determined by the type and size of the items to be stored within it. In the preferred embodiment for a first aid kit, the length of tube 12 is approximately 6" and the diameter of the tube is approximately 2". Preferably, tube 12 is extruded from clear plastic and has a side wall thickness sufficient to protect the stored items while being flexible enough for easy storage. In the preferred embodiment for a first aid kit, this wall thickness is approximately 0.2". The clear plastic tube can receive a paper circular sleeve which identifies the contents of the kit and is slightly deformable to better conform to irregular shapes in the area around the tube.

End cap 13 is preferably plastic and has a circular base 18 and a skirt or rim 19 around the outside perimeter of base 18. Skirt 19 extends from base 18 of cap 13 to receive and hold the end of tube 12. The tolerance between the inside diameter of the skirt 19 and the outside diameter of tube 12 is selected so skirt 19 is frictionally secured on the end of tube 12. Skirt 19 is sufficiently long enough to prevent the inadvertent removal of cap 13 from tube 12 and in the preferred embodiment is approximately ¼ of an inch.

Figure 2:
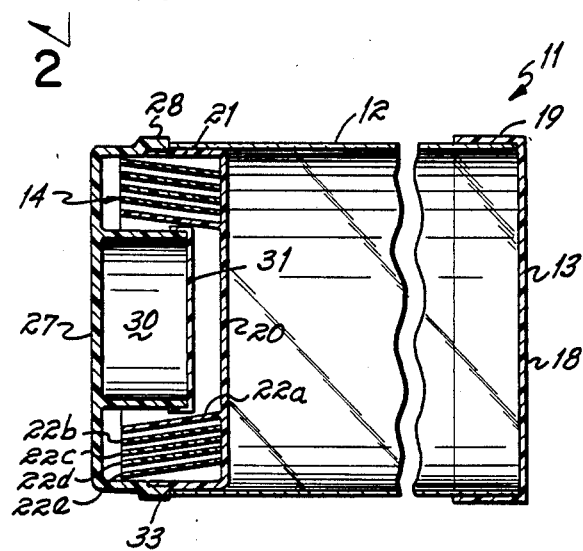
FIG. 2 is a cross sectional view, partly broken away, taken along line 2—2 of FIG. 1.
Figure 3:
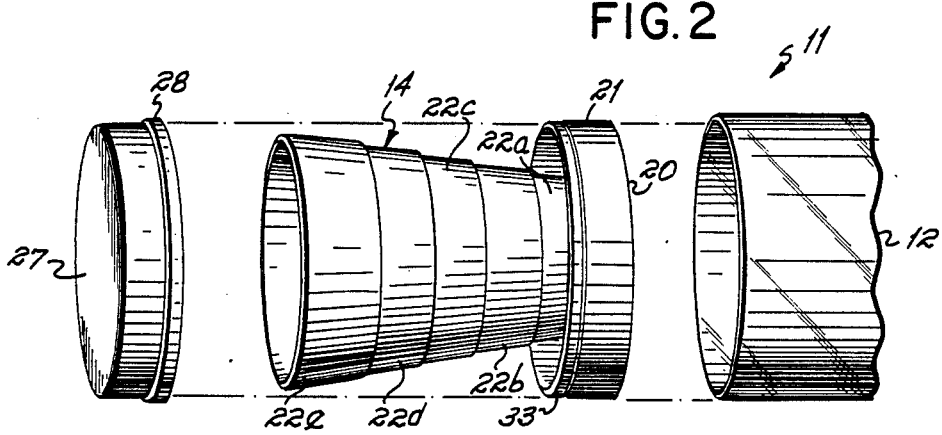
FIG. 3 is an exploded perspective view of the collapsible cup and the end of the tube.

As shown in FIGS. 2 and 3, collapsible cup 14 has a base 20 with a circular rim 21. Connected to base 20 are a plurality of annular cup segments of graduated diameters designated as 22a–22e. The smallest diameter segment 22a extends integrally from the base, see FIG. 2. When collapsed, the annular segments 22 lie concentrically against base 20 and within the perimeter of rim 21. A cup cover 27 is provided to protect and enclose annular cup segments 22 when cup 14 is collapsed upon its base 20. Cover or lid 27 has an outwardly offset flange or skirt 28 at its edge which surrounds rim 21 and abuts a lip or stop 33 cut in the upper portion of rim 21. Preferably, stop 33 is placed approximately 0.1" from the edge of rim 21.

As shown in FIG. 2, the outside diameter of rim 21 is slightly less than the inside diameter of tube 12. Thus, tube 12 receives cup base 20 with connected annular cup segments 22, which thereby closes this end of tube 12. Flange 28 has a diameter which is slightly larger than the outer diameter of rim 21 so as to receive and hold rim 21 of base 20 at stop 33. Flange 28 is also thick enough to abut tube 12 at the end in which the collapsed cup is inserted and is preferably 0.05". Thus, flange 28 acts as a stop to prevent the cup from being seated in tube 12 beyond the point at which the flange abuts the tube end.

In the preferred embodiment of the first aid kit depicted in FIG. 2, cover 27 has an integral pill container 30 which provides a special repository for pills and the like. Pill container 30 is formed on cover 27 and fits within the smallest annular segment 22a when cup 14 is collapsed and cover 27 is placed over the annular segments 22. Pill container 30 is cylindrical and centered on cover 27. Pills placed in pill container 30 are retained by a cap 31 which frictionally fits over pill container 30. Collapsible cups of this configuration are known per se, but so far as is known to me, they have not heretofore been used to provide a end closure for a container.

When the contents of the container are needed, collapsible cup 14 is removed from tube 12 as shown in FIG. 3, or the outer end cap 13 can be removed from tube 12. Removal of either cap provides access to the items within the tube 12. To use the cup, it is removed from the end of tube 12 and cover 27 is separated from base 20. Outermost annular cup segment 22e is then gripped and pulled away from base 20. This extension causes connected graduated annular cup segments 22 to extend from base 20 to form a liquid tight vessel. If pills within pill container 30 are to be administered, cap 31 is removed from pill container 30 and the pills taken from pill container 30.

The container described above is not limited to use in first aid kits but could be used to store camping equipment, tools, emergency food or the like. The description of the preferred embodiment given above should be considered illustrative in all respects and not restrictive of the invention as defined by the appended claims.

What is claimed is:

1. A storage container comprising:
    a tube having a side wall and first and second end openings;
    a closure for said first end opening;
    a collapsible cup comprising a base with a rim, a series of annular cup segments of graduated diameters which are extendible to form a cup, the segment of smallest diameter being joined to said base, the segments being collapsible onto said base around the smallest segment, inwardly of said rim; and
    a cover for said cup, said cover having a skirt which removably fits onto said rim of said base of said cup when said cup is collapsed, one of said rim and skirt being sized to frictionally fit within said second opening to form a removable closure for said second opening.

2. The storage container of claim 1 wherein a pill container mounted to said cover, said pill container nesting within said cup segments when they are collapsed.

3. The storage container of claim 2 wherein said pill container has a removable cap.

4. The storage container of claim 3 wherein said rim of said base of said cup has a stop; and
    said cover has a flange which abuts said stop of said rim.

5. The storage container of claim 1 wherein said closure for said first end opening has a base and a skirt around said base, said skirt fitting onto said tube around said first end opening.

6. The storage container of claim 1 wherein said tube is a transparent plastic tube.

7. A storage kit, the kit comprising:
    a cover having a circular base and a rim extending from a circumference of said circular base;
    a tube having a side wall and a first and a second opening, said side wall being received within said rim of said cover to form a receptacle from said side wall of said tube and said circular base for storing a plurality of items;
    a collapsible cup; and
    a lid, said lid having a lip to receive and secure said collapsible cup, said lid with said collapsible cup being inserted into said second opening of said tube to secure said plurality of items stored within said tube and to provide a cup for use with said plurality of items when said collapsible cup is removed from said second opening and said lid is removed from said collapsible cup.

* * * * *